United States Patent [19]

Stoutamire

[11] Patent Number: 4,546,198

[45] Date of Patent: Oct. 8, 1985

[54] ASYMMETRIC SYNTHESIS OF ESTERS AND ACIDS

[75] Inventor: Donald W. Stoutamire, Modesto, Calif.

[73] Assignee: Shell Oil Company, Houston, Tex.

[21] Appl. No.: 593,153

[22] Filed: Mar. 26, 1984

Related U.S. Application Data

[63] Continuation-in-part of Ser. No. 458,813, Jan. 18, 1983.

[51] Int. Cl.⁴ .................... C07C 69/76; C07B 19/00; C07B 20/00
[52] U.S. Cl. ........................................ 560/105; 560/9; 560/11; 560/61; 560/100; 560/147; 560/149; 560/152; 562/401; 562/426; 562/429; 562/471; 562/490; 562/494; 562/507
[58] Field of Search .............. 562/401, 426, 429, 471, 562/490, 494, 507; 560/105, 9, 11, 61, 100, 147, 149, 152

[56] References Cited

FOREIGN PATENT DOCUMENTS 63731 11/1982 European Pat. Off. ............ 560/105

OTHER PUBLICATIONS

Jähme et al., *Angew. Chem. Int. Ed. Engl.*, 20 (10), pp. 885–887, (1981).
C.A. 58:12479f, (1963).
*Organic Reactions*, R. Adams, editor, John Wiley & Sons, Inc., New York, 1946, pp. 124–127.

*Primary Examiner*—Paul J. Killos

[57] ABSTRACT

Stereoisomerically-enriched esters are prepared by treating a non-symmetrical ketene with a racemic or chiral tertiary-base-substituted alkylcarbinol. Optional hydrolysis of the esters gives the corresponding optically-active carboxylic acids corresponding to the non-symmetrical ketene.

22 Claims, No Drawings

ASYMMETRIC SYNTHESIS OF ESTERS AND ACIDS

CROSS-REFERENCE TO RELATED APPLICATIONS

This application is a continuation-in-part of Ser. No. 458,813 filed Jan. 18, 1983.

BACKGROUND OF THE INVENTION

1. Field of the Invention

The present invention relates to a process for the asymmetric synthesis of esters and to the preparation of the corresponding optically-active acids.

2. Description of the Prior Art

It is known that chiral secondary alcohols can react with non-symmetrical ketenes to give asymmetric esters by the addition of an achiral base. Clearly, these processes require the use of materials which are not incorporated into the product itself.

SUMMARY OF THE INVENTION

The present invention is directed to a process for the preparation of an optically-active ester, or a mixture enriched therein, which comprises reacting a non-symmetrical ketene with a racemic or optically-active, tertiary-base-substituted alkylcarbinol. In this application "tertiary-base-substituted" is intended to refer to a basic tertiary-nitrogen substituent, moiety or functional group.

Depending on the reactants selected, the product ester of the process of the invention is an ester enriched in one of its optically-active diastereomers or enriched in one enantiomer pair, the enrichment being over an equimolar amount of diastereomer(s) expected from a reaction of an equimolar amount of a non-symmetrical ketene with a racemic or optically-active tertiary-base-substituted alkylcarbinol.

The reaction is conducted in the presence or absence of a solvent. When a solvent is used the solvent is preferably a non-hydroxylic solvent such as hydrocarbons, chlorinated hydrocarbons, ethers and the like. For example, suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between 40° and 65° C., between 60° and 80° C. or between 80° and 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Suitable chlorinated hydrocarbons contain from 1 to 4 chlorine atoms in combination with an alkane chain containing from 1 to 4 carbon atoms or with a benzene ring, for example, carbon tetrachloride, chloroform, dichloromethane, 1,2-dichloroethane, trichloroethane, perchloroethane, chlorobenzene and 1,2- or 1,3-dichlorobenzene and the like. Ethers are generally those containing from 4 to 6 carbon atoms such as diethyl ether, methyl tert-butyl ether and diisopropyl ether and the like. Preferably, the reaction is conducted in the presence of toluene.

Any non-symmetrical ketene is useful (provided it does not contain substituent groups which form other stable reaction products with the optically-active, base-substituted alkylcarbinol. The non-symmetrical ketene has the formula I

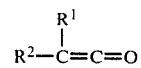

wherein $R^1$ and $R^2$ each independently is a different alkyl group containing from 1 to 10 carbon atoms or a cycloalkyl group containing 3 to 7 ring carbon atoms, or $R^2$ is also an alkenyl or alkynyl group containing 2 to 10 carbon atoms; a naphthyl group, a phenyl group, a heterocyclic group containing 5 or 6 ring atoms, one of which is oxygen, sulfur or nitrogen, and the remainder are carbon atoms; or is an amino group disubstituted by acyl or alkyl containing up to 10 carbon atoms or a phenyl group; or $R^1$ and $R^2$, when taken together with the carbon atom to which they are attached, form a non-symmetrical cycloalkyl group containing 4 to 7 ring carbon atoms and 4 to 14 carbon atoms. The $R^1$ and $R^2$ groups can be optionally substituted by one or more of halogen atoms having an atomic number of from 9 to 35, alkyl or haloalkyl containing 1 to 4 carbon atoms, alkenyl or haloalkenyl containing 2 to 4 carbon atoms, haloalkoxy or alkoxy of 1 to 4 carbon atoms, haloalkylthio or alkylthio of 1 to 4 carbon atoms or equivalent kinds and sizes of substituents which may contain the same or greater carbon number.

One embodiment of non-symmetrical ketenes used in the process of the invention is that which results in pyrethroid esters, including those esters having an acid moiety described in U.S. Pat. Nos. 4,062,968, and 4,199,595. Examples of such ketenes include those having the formula I in which $R^1$ is isopropyl or cyclopropyl optionally substituted by one or more chlorine atoms; $R^2$ is an alkyl group containing 1 to 6 carbon atoms; an alkenyl group containing 2 to 6 carbon atoms; a naphthyl group, a phenyl group, a phenyl group or a (benzyloxycarbonyl)phenylamino group, each optionally ring-substituted by one or more of halogen, alkyl, haloalkyl, alkoxy, haloalkoxy in which the halogens are bromine, chlorine or fluorine, and the alkyl groups contain 1 or 4 carbon atoms.

Of particular interest as non-symmetrical ketene reactants because their pyrethroid esters are usually highly pesticidally active are those ketenes having the formula I in which $R^1$ is isopropyl; $R^2$ is a phenyl group para-substituted by halogen, alkyl, haloalkoxy, in which the halogen is e.g. chlorine or fluorine and the alkyl contain 1 to 4 carbon atoms, e.g. methyl.

For example, the non-symmetrical ketene is (4-chlorophenyl)isopropylketene, (4-(difluoromethoxy)-phenyl)isopropylketene, or (4-trifluoromethyl-3-chlorophenyl)(benzyloxycarbonyl)amino)isopropylketene, and the like.

Any racemic or optically-active, tertiary-base-substituted alkylcarbinol can be used (provided it does not contain substituent groups which form other stable reaction products with ketenes). For example, the carbinol is an aliphatic, alicyclic, aromatic or heterocyclic base-substituted carbinol containing from about 1 to 20 carbon atoms, preferably 12 carbon atoms. These optically-active, base-substituted carbinols are conventional kinds of materials known in the art, and can be prepared by known methods of direct synthesis and/or resolution. For example, numerous optically-active, base-substituted carbinols are specifically disclosed in Newman, P., "Optical Resolution Procedures for Chemical Compounds", Vol. 1, Amines and Related Compounds, Optical Resolution Information Center, Manhattan College, Riverdale, NY, Library of Congress Catalog No. 78-61452.

Non-limiting examples of tertiary-base-substituted alkylcarbinols include, 1-(dimethylamino)-2-propanol, 1-(dimethylamino)-2-butanol, 3-(dimethylamino)-2-butanol, 1-(diethylamino)-2-propanol, alpha-methyl-2-pyridinylmethanol, alpha-methyl-3-pyridinylmethanol, alpha-methyl-4-pyridinylmethanol, alpha-ethyl-2-pyridinylmethanol, alpha-methyl-2-pyridinylethanol, N-methylephedrin and the like.

One embodiment of optically-active, tertiary-base-substituted alkylcarbinols comprises compounds of the formula II

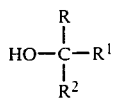

wherein R is an alkyl group containing 1 to 4 carbon atoms; $R^1$ is different from R and is a hydrogen atom or an alkyl group containing from 1 to 10 carbon atoms; and $R^2$ is a nitrogen-heterocyclic group containing up to 10 carbon atoms; or a tertiary-base-substituted alkyl, alkenyl, cycloalkyl, aralkyl or aryl group in which the tertiary-base-substituent is a nitrogen-heterocyclic group containing up to 10 carbon atoms or an amino group —$NR^3R^4$ in which $R^3$ and $R^4$ each independently is an alkyl group of 1 to 4 carbon atoms or a phenyl group. The tertiary-base is preferably a group —$NR^3R^4$ as defined above or is a nitrogen-heterocyclic group. For example, the nitrogen heterocyclic group contains 4 to 10 carbon atoms and 1 to 3 nitrogen atoms and 0 to 1 sulfur or oxygen atoms in the ring, such as pyridinyl, N-methylpyridinyl, 1-isoquinolinyl, 2-quinolinyl, triazolyl, thiadiazolyl, imidazolyl, pyrrolyl, N-methylimidazolyl, N-methylpyrazolyl, isoxazolyl, oxazolyl, isothiazolyl, thiazolyl and the like. Preferably, R is an alkyl group containing 1 or 2 carbon atoms, i.e., a methyl or ethyl group; $R^1$ is a hydrogen atom or an alkyl group different from R and containing 1 or 2 carbon atoms; $R^2$ is a nitrogen-heterocyclic group containing up to 10 carbon atoms or a tertiary-base-substituted alkyl group containing 1 to 10 carbon atoms substituted by an amino group —$NR^3R^4$ in which $R^3$ and $R^4$ each independently is an alkyl of 1 to 4 carbon atoms or phenyl, such as (dimethylamino)methyl, 1-(dimethylamino)ethyl or (diethylamino)methyl and the like; or $R^2$ is a 3-pyridinyl group.

The reaction is conducted by adding the non-symmetrical ketene to the racemic or optically-active, tertiary-base-substituted alkylcarbinol, which may be dissolved in a solvent, agitating the mixture, e.g., by stirring, and maintaining the reaction conditions for an amount of time to effect the formation of the diastereomerically enriched or optically-active ester. Separation and recovery of the optically-active ester products are achieved by conventional techniques used for separating diastereoisomers, including chromatographic separations and the like.

The molar ratios of the starting materials, non-symmetrical ketene and racemic or optically-active, tertiary-base-substituted alkylcarbinol can vary. For example, the molar ratio of ketene to carbinol is suitably from about 10:1 to about 1:10 and, preferably, from about 5:1 to about 1:5. However, it is desirable to have approximately equimolar amounts of ketene to carbinol of from about 1:1 to about 1:1.1.

The temperature of the reaction as well as the pressure can vary. At normal pressures, the temperature is from about −10° C. to about 50° C., more or less. Ambient temperatures of about 15° C. to about 35° C. are convenient.

Another embodiment of the present invention is directed to a process for the preparation of an optically-active carboxylic acid which comprises reacting a non-symmetrical ketene with an optically-active (chiral), tertiary-base-substituted carbinol followed by separation of the resulting ester diastereoisomers and hydrolysis of the resulting ester diastereoisomer to yield the optically-active carboxylic acid corresponding to the non-symmetrical ketene.

The process conditions for formation of the ester are the same as described above as are the non-symmetrical ketene and optically-active, tertiary-base-substituted alkylcarbinol. It is desirable, however, that the non-symmetrical ketene and the optically-active, tertiary-base-substituted alkylcarbinol be of dissimilar molecular weights so that upon hydrolysis the desired optically-active carboxylic acid can be separated and recovered by conventional techniques, such as distillation, extraction, crystallization and the like.

Again, any pair of ester diastereoisomer formed from the non-symmetrical ketene reaction with the optically-active, tertiary-base-substituted alkylcarbinol are separated by conventional techniques used for separating diastereoisomers, e.g., chromatographic separation and the like.

The hydrolysis is conducted in the presence of water or source of water and under conditions conventional for hydrolysis of esters. Conveniently, the hydrolysis is conducted at ambient temperature or above with an aqueous acid, such as mineral acids, including hydrochloric acid or the like. If a solvent is used in the hydrolysis, it is conveniently any used in the step of forming the ester.

Thus, the process is useful for preparing any optically-active carboxylic acids that are acyclic, alicyclic, aromatic or heteroaromatic. Preferably, the acid product has the formula III

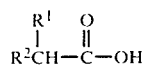

wherein $R^1$ and $R^2$ are different, each independently is an alkyl, aralkyl, alkoxy, aryloxy, alkylthio, alkylsulfonyl, arylthio, or arylsulfonyl group containing from 1 to 10 carbon atoms or a cycloalkyl group containing 3 to 7 ring carbon atoms, or when taken together with the carbon atom to which they are attached form a non-symmetrical cycloalkyl group containing 4 to 7 ring carbon atoms; $R^2$ is also an alkenyl or alkynyl containing from 2 to 10 carbon atoms, a naphthyl group, a phenyl group, a heterocyclic group containing 5 or 6 ring atoms, one of which is oxygen, sulfur or nitrogen, and the remainder are carbon atoms or is an amino group disubstituted by acyl or alkyl containing up to 10 carbon atoms or a phenyl group. The $R^1$ and $R^2$ groups can be optionally substituted by one or more of halogen of atomic numbers 9 to 35, an alkyl, haloalkyl or cycloalkyl group containing up to 7 carbon atoms, alkenyl or haloalkenyl group of 2 to 4, haloalkoxy or alkoxy group of 1 to 4 carbon atoms, haloalkylthio or alkylthio group of 1 to 4 carbon atoms or equivalent kinds of substituents.

One embodiment of acid products are pyrethroid acids, including those of U.S. Pat. Nos. 4,062,968 or 4,199,595. Examples of such acid include those having the formula III in which $R^1$ is isopropyl or cyclopropyl, optionally substituted by one or more chlorine atoms; $R^2$ is an alkyl group containing 1 to 6 carbon atoms; an alkenyl group containing 2 to 6 carbon atoms; a naphthyl group, a phenyl group or a (benzyloxycarbonyl)phenylamino group, each optionally ring-substituted by one or more of halogen, alkyl, haloalkyl, alkoxy, haloalkoxy in which the halogens are bromine, chlorine or fluorine and the alkyl groups contain 1 or 4 carbon atoms. For example, the acid is isopropyl(4-chlorophenyl)acetic, isopropyl(4-(difluoromethoxy)phenyl)acetic or isopropyl((4-trifluoromethyl-3-chlorophenyl)-(benzyloxycarbonyl)amino)acetic and the like.

Preferably, in formula III, $R^1$ is isopropyl and $R^2$ is a phenyl group optionally substituted by halogen, an alkyl or haloalkyl group of 1 to 4 carbon atoms or an alkoxy or haloalkoxy group containing 1 to 4 carbon atoms, preferably at the para position, especially useful are 4-chlorophenyl, 4-(difluoromethoxy)phenyl, 4-methylphenyl, 4-tert-butylphenyl and the like. $R^2$ is preferably 4-chlorophenyl. For example, the acid product is S-isopropyl-(4-(difluoromethoxy)phenyl)acetic or especially S-isopropyl-4-chlorophenylacetic acid.

The non-symmetrical ketenes used in the processes of the invention are generally known in the art or are novel. Ketenes used in the present invention can be prepared by treating the corresponding acid halide with a tertiary amine.

Tertiary amines can be any alkyl, aryl or heterocyclic nitrogen base including mono- or polyamines and the like. Preferably, the tertiary amine is an amine in which any alkyl groups contain from 1 to 10 carbon atoms, any aryl or aralkyl groups contain from 6 to 20 carbon atoms and 1 to 2 hydrocarbyl rings, and any heterocyclic amines contain at least one ring nitrogen atom in a 5 or 6 membered heterocyclic ring optionally containing a sulfur or oxygen atom or another nitrogen atom. It desirably contains three alkyl groups of 1 to 4 carbon atoms, for example: trimethylamine, tri-n-propylamine, and especially triethylamine or trimethylamine.

The reaction is conducted in the presence or absence of a solvent. When a solvent is used the solvent is preferably a non-hydroxylic solvent such as hydrocarbons, chlorinated hydrocarbons, ethers and the like. For example, suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between 40° and 65° C., between 60° and 80° C. or between 80° and 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Suitable chlorinated hydrocarbons contain from 1 to 4 chlorine atoms in combination with an alkane chain containing from 1 to 4 carbon atoms or with a benzene ring, for example, carbon tetrachloride, chloroform, dichloromethane, 1,2-dichloroethane, trichloroethane, perchloroethane, chlorobenzene and 1,2- or 1,3-dichlorobenzene and the like. Ethers are generally those containing from 4 to 6 carbon atoms such as diethyl ether, methyl tert-butyl ether and diisopropyl ether and the like. Tetrahydrofuran and dioxane are also useful.

In the preparation of the non-symmetrical ketene, the molar ratio of the starting materials can be varied widely. For example, the molar ratio of acid halide to tertiary amine is from about 10:1 to about 1:10, and preferably from about 5:1 to about 1:5. However, it is desirable to have a molar excess of base to acid halide. Therefore, a molar ratio of acid halide to base is desirably from about 1:1 to about 1:5 and conveniently from about 1:1.2 to about 1:2.

In the preparation of the non-symmetrical ketene, the temperature can be varied widely. At normal pressure, for example, the temperature of reaction can be varied but is preferably, for example, from about 10° C. to 40° C. more or less, although higher temperatures of about 75° C. to about 95° C. have been found very useful.

Separation and recovery of the product ketene are achieved by conventional methods, including crystallization and the like.

One process for preparing non-symmetrical ketenes is from any corresponding acid halides which do not contain substituted groups which would react with the tertiary amine. For example, the acid halide can be that of an acyclic, alicyclic, aromatic or heteroaromatic acid. Preferably, the acid halide has the formula IV

wherein X is the halogen atom, such as chlorine or bromine, $R^1$ and $R^2$ each independently is an alkyl, aralkyl, alkoxy, aryloxy, alkylthio, alkylsulfonyl, arylthio or arylsulfonyl group containing from 1 to 10 carbon atoms or a cycloalkyl group containing 3 to 7 ring carbon atoms, or when taken together with the carbon atom to which they are attached form a non-symmetrical cycloalkyl group containing 4 to 7 ring carbon atoms; $R^2$ is also an alkenyl or alkynyl containing from 2 to 10 carbon atoms, a naphthyl group, a phenyl group, a heterocyclic group containing 5 or 6 ring atoms, one of which is oxygen, sulfur or nitrogen, and the remainder are carbon atoms or is an amino group disubstituted by acyl or alkyl containing up to 10 carbon atoms or a phenyl group. The $R^1$ and $R^2$ groups can be optionally substituted by one or more of halogen of atomic numbers 9 to 35, an alkyl, haloalkyl or cycloalkyl group containing up to 7 carbon atoms, alkenyl or haloalkenyl group of 2 to 4, haloalkoxy or alkoxy group of 1 to 4 carbon atoms, haloalkylthio or alkylthio group of 1 to 4 carbon atoms or equivalent kinds of substituents.

One embodiment of acid halides are halides of pyrethroid acids, including those of U.S. Pat. No. 4,062,968 or 4,199,595. Examples of such acid halides include those having the formula IV in which $R^1$ is isopropyl or cyclopropyl, optionally substituted by one or more chlorine atoms; $R^2$ is an alkyl group containing 1 to 6 carbon atoms; an alkenyl group containing 2 to 6 carbon atoms; a naphthyl group, a phenyl group or a (benzyloxycarbonyl)phenylamino group, each optionally ring-substituted by one or more of halogen, alkyl, haloalkyl, alkoxy, haloalkoxy in which the halogens are bromine, chlorine or fluorine and the alkyl groups contain 1 or 4 carbon atoms. For example, the acid halide is isopropyl-(4-chlorophenyl)acetyl chloride, isopropyl(4-(difluoromethoxy)phenyl)acetyl chloride, or isopropyl-((4-(-trifluoromethyl)-3-chlorophenyl)(benzyloxycarbonyl)amino)acetyl chloride, and the like.

Preferably, in formula IV, $R^1$ is isopropyl and $R^2$ is a phenyl group optionally substituted by halogen, an alkyl or haloalkyl group of 1 to 4 carbon atoms or an alkoxy or haloalkoxy group containing 1 to 4 carbon atoms, preferably at the para position, especially useful are 4-chlorophenyl, 4-(difluoromethoxyphenyl,4-methylphenyl, 4-tert-butylphenyl and the like. Many of the non-symmetrical ketenes of the invention are known in the art per se, for example, (4-chlorophenyl)isopropylketene as in U.S. Pat. No. 4,199,527. Some other non-symmetrical ketenes are believed to be novel, for example, including (4-(difluoromethoxy)phenyl)isopropylketene.

The ester products are known, per se, or are useful in preparing the optically-active acids, which themselves are known, per se, and are useful as or intermediates to pharmaceuticals, herbicides, pesticides and the like, for example, as in U.S. Pat. Nos. 3,686,183, 3,452,079, 4,009,283, 4,335,251 and British Pat. No. 4,014,137 and the like.

ILLUSTRATIVE EMBODIMENTS

The following embodiments are provided for the purpose of illustrating the invention and should not be regarded as limiting it in any way. The identity of the products was confirmed by infrared and nuclear magnetic resonance spectral analyses as necessary.

EMBODIMENT 1

(4-Chlorophenyl)isopropylketene

To a solution of 2.31 g of isopropyl(4-chlorophenyl)acetyl chloride in 10 ml of methylene chloride was added in one portion 1.5 g of triethylamine. After 18 hours, 15 ml of heptane was added to the mixture and the triethylamine hydrochloride removed by filtration. The filtrate was stripped and 10 ml of heptane was added and the resulting mixture was filtered and stripped to give a yellow residue, which was dissolved in 5 ml heptane for GLC analysis. The resulting solution was distilled through a Bantam-ware short-neck head from an oil bath at 125°–150° C. and head temperature of 110°–100° C. at 0.2–0.05 mm to give 0.95 g of distillate and 0.81 g of gum. The distillate was crystallized twice from 2 volumes of hexane at −80° C. The solid was melted and stripped to about 40° C. at 0.5 mm to give 0.42 g of the desired product as a yellow liquid.

EMBODIMENT 2

(4-Chlorophenyl)isopropylketene

A sample of 53.2 g of isopropyl(4-chlorophenyl)acetic acid was treated with 21.5 ml of thionyl chloride in a 500 ml flask and heated slowly to 80° C. and maintained at 80° C. for 20 minutes. The reaction mixture was allowed to stand at room temperature for 2 days. The volatiles were stripped to 75° C. at 0.5 mm Hg. The resulting yellow liquid was diluted with 250 ml of methylene chloride followed by addition of 38.0 g of triethylamine. The mixture was stirred until triethylamine hydrochloride began to precipitate after 30 minutes. After 16 hours, the reaction mixture was filtered and solid triethylamine hydrochloride was washed with heptane. Most of the solvent was stripped from the filtrate by rotary evaporation at 50° C. The residue was diluted with 75 ml of heptane and additional triethylamine hydrochloride was removed by filtration as above. The filtrate was restripped and rediluted with 75 ml heptane and refiltered with the aid of 25 ml of heptane. The filtrate was cooled in dry ice, seeded and crystallized. The resulting crystals were filtered with a filter stick and washed with chilled heptane. The filtered solids were melted, diluted with one-half volume heptane, crystallized at −80° C. and the collected solid was melted and stored at −80° C. The filtrate solution was warmed, stripped of most solvent, then distilled through a Bantam were short path head at 0.05 to 0.06 mm Hg from an oil bath at 90°–120° C. Total distillate was 14.5 g collected as a bright yellow-orange liquid at a head temperature of 60°–85° C. The distillate was crystallized from an equal volume of pentane at −80° C., filtered and washed twice with heptane as above to give, on warming, a second melt. The stripped filtrates totalling 5.79 g were crystallized as above in a 6-inch test tube and the melt was recrystallized immediately as described above to give a third melt. The three melts were combined and stripped to 50° C. at 5 mm Hg to give 29.4 g of the desired ketene as a yellow liquid.

EMBODIMENT 3

(4-Chlorophenyl)isopropylketene

To 57.75 g of isopropyl(4-chlorophenyl)acetyl chloride was added 69.4 ml of triethylamine. The mixture was allowed to stand overnight at 20° C. The resulting mushy solid was crushed, diluted with 300 ml of redistilled hexane and filtered. The solids were washed three times with 75 ml of hexane, filtered and dried by suction with calcium chloride dried air to give 32 g triethylamine hydrochloride. The combined hexane solutions of ketene slowly deposited additional solids; the mixture was let stand at room temperature overnight with the flask wrapped in aluminum foil and filtered again to give 0.75 g of additional solids. The solvent was removed from the filtrate by rotary evaporation, then taken briefly to 1 mm Hg. To the mixture was added 500 ml of hexane, and after filtration, the filtrate was stripped to a yellow oil. This oil was distilled through a Bantam-ware short path head at 0.5 mm Hg to give 28.61 g of the desired ketene as a yellow liquid, $d^{20}$ 1.10.

EMBODIMENT 4

(4-(Difluoromethoxy)phenyl)isopropylketene

Following procedures similar to those described in Embodiment 3 above, the desired product is prepared by treating isopropyl(p-(difluoromethoxy)phenyl)acetyl chloride with triethylamine.

EMBODIMENT 5

1-(Dimethylamino)-2-propyl Isopropyl-(4-chlorophenyl)acetate

A 1 dram vial fitted with a septum cap was charged with 0.69 g of toluene followed by 1.08 g of optically-active 1-(dimethylamino)-2-propanol. The resulting mixture was chilled with ice and then 0.196 g of (4-chlorophenyl)isopropylketene was injected. The reaction temperature rose slowly to 30° C. The color discharged after 1.25 hours at room temperature. The reaction product was separated by gas liquid chromatography to give the desired product in a diastereomer ratio of 25.6% of isomer pair 1 and 74.4% of isomer pair 2.

EMBODIMENT 6

1-(Dimethylamino)-2-propyl alpha-Isopropyl-4-chlorophenylacetate and Isopropyl-(4-chlorophenyl)acetic Acid A 1 dram vial fitted with a septum cap is charged with 0.69 g of toluene followed by 1.08 g of optically-active 1-(dimethylamino)-2-propanol. The resulting mixture is chilled with ice and then 0.196 g of (4-chlorophenyl)isopropylketene is injected. The reaction temperature is raised slowly to 30° C. until the color discharges (after 1.25 hours at room temperature). The reaction product is separated by gas liquid chromatography to give the desired enriched ester product in a stereomer ratio of 25.6% of isomer 1 and 74.4% of isomer 2.

After the two diastereoisomers are separated by chromatographic separation, then each of the resulting single diastereoisomer esters is hydrolyzed with acetic acid to give the corresponding S-isopropyl-(4-chlorophenyl)acetic acid and R-isopropyl-(4-chlorophenyl)acetic acid, but in different amounts because of the asymmetric induction.

What is claimed is:

1. A process for the preparation of an optically-active ester or a mixture enriched therein which comprises reacting a non-symmetrical ketene with a racemic or an optically-active, tertiary-base-substituted alkylcarbinol.

2. A process according to claim 1 wherein the racemic or optically-active, tertiary-base-substituted alkylcarbinol is an aliphatic, alicyclic, aromatic or heterocyclic alkylcarbinol containing from 1 to 20 carbon atoms.

3. A process according to claim 2 wherein the alkylcarbinol contains from 1 to 12 carbon atoms.

4. A process according to claim 3 wherein the alkylcarbinol has the formula

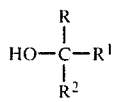

wherein R is an alkyl group containing 1 to 4 carbon atoms; $R^1$ is different from R and is a hydrogen atom or an alkyl group containing from 1 to 10 carbon atoms; and $R^2$ is a nitrogen-heterocyclic group containing up to 10 carbon atoms; or is a tertiary-base-substituted alkyl, alkenyl, cycloalkyl, aralkyl or aryl group in which the tertiary-base-substituent is a nitrogen-heterocyclic group containing up to 10 carbon atoms or an amino group —$NR^3R^4$ in which $R^3$ and $R^4$ each independently is an alkyl group of 1 to 4 carbon atoms or a phenyl group.

5. A process according to claim 4 wherein R is an alkyl group containing 1 or 2 carbon atoms; $R^1$ is a hydrogen atom or an alkyl group different from R and containing 1 or 2 carbon atoms; $R^2$ is a tertiary-base-substituted alkyl group containing 1 to 10 carbon atoms substituted by an amino group —$NR^3R^4$ in which $R^3$ and $R^4$ each independently is an alkyl group containing 1 to 4 carbon atoms or a phenyl group; or $R^2$ is a 3-pyridinyl group.

6. A method according to claim 5 wherein the alkylcarbinol is 1-dimethylamino-2-propanol.

7. A process according to claim 1 wherein the non-symmetrical ketene has the formula

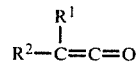

$R^1$ is isopropyl or cyclopropyl optionally substituted by one or more chlorine atoms; $R^2$ is an alkyl group containing 1 to 6 carbon atoms; an alkenyl group containing 2 to 6 carbon atoms; a naphthyl group, a phenyl group or a (benzyloxycarbonyl)phenylamino group each optionally ring substituted by one or more of halogen, alkyl, haloalkyl, alkoxy, haloalkoxy in which the halogens are bromine, chlorine or fluorine and the alkyl or cycloalkyl group contains 1 or 4 carbon atoms.

8. A process according to claim 7 wherein in the non-symmetrical ketene $R^1$ is isopropyl; $R^2$ is a phenyl group para-substituted by halogen, alkyl, haloalkoxy in which the halogen is chlorine or fluorine and the alkyl contains 1 to 4 carbon atoms.

9. A process according to claim 8 wherein the non-symmetrical ketene is (4-chlorophenyl)isopropylketene, (4-(difluoromethoxy)phenyl)isopropylketene, or ((4-trifluoromethyl-3-chlorophenyl)(benzyloxycarbonyl)amino)isopropylketene.

10. A process according to claim 1 wherein the non-symmetrical ketene is prepared by treating an acid halide with a tertiary amine.

11. A process according to claim 1 wherein the acid halide is isopropyl-(4-chlorophenyl)acetyl chloride.

12. A process for the preparation of an optically-active carboxylic acid which comprises reacting a non-symmetrical ketene with an optically-active, tertiary-base-substituted alkylcarbinol followed by separation of the ester diastereoisomers and hydrolysis of the resulting ester diastereoisomer to yield the optically-active carboxylic acid.

13. A process according to claim 12 wherein the optically-active, tertiary-base-substituted alkylcarbinol is an aliphatic, alicyclic, aromatic or heterocyclic carbinol containing from 1 to 20 carbon atoms.

14. A process according to claim 13 wherein the alkylcarbinol contains from 1 to 12 carbon atoms.

15. A process according to claim 14 wherein the alkylcarbinol has the formula

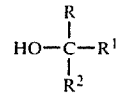

wherein R is an alkyl group containing 1 to 4 carbon atoms; $R^1$ is different from R and is a hydrogen atom or an alkyl group containing from 1 to 10 carbon atoms; and $R^2$ is a nitrogen-heterocyclic group containing up to 10 carbon atoms; or a tertiary-base-substituted alkyl, alkenyl, cycloalkyl, aralkyl or aryl group in which the tertiary-base-substitutent is a nitrogen-heterocyclic group containing up to 10 carbon atoms or an amino group —$NR^3R^4$ in which $R^3$ and $R^4$ each independently is an alkyl group of 1 to 4 carbon atoms or a phenyl group.

16. A process according to claim 15 wherein R is an alkyl group containing 1 or 2 carbon atoms; $R^1$ is a hydrogen atom or an alkyl group different from R and containing 1 or 2 carbon atoms; $R^2$ is a tertiary-base-substituted alkyl group containing 1 to 10 carbon atoms substituted by an amino group —$NR^3R^4$ in which $R^3$ and $R^4$ each independently is an alkyl group containing 1 to 4 carbon atoms or a phenyl group; or $R^2$ is a 3-pyridinyl group.

17. A method according to claim 16 wherein the optically-active, tertiary-base-substituted alkylcarbinol is 1-dimethylamino-2-propanol.

18. A process according to claim 12 wherein the non-symmetrical ketene has the formula

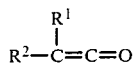

$R^1$ is isopropyl or cyclopropyl optionally substituted by one or more chlorine atoms; $R^2$ is an alkyl group containing 1 to 6 carbon atoms; an alkenyl group containing 2 to 6 carbon atoms; a naphthyl group, a phenyl group or a (benzyloxycarbonyl)phenylamino group each optionally ring substituted by one or more of halogen, alkyl, haloalkyl, alkoxy, haloalkoxy in which the halogens are bromine, chlorine or fluorine and the alkyl or cycloalkyl group contains 1 or 4 carbon atoms.

19. A process according to claim 18 wherein in the non-symmetrical ketene $R^1$ is isopropyl; $R^2$ is a phenyl group para-substituted by halogen, alkyl, haloalkoxy in which the halogen is chlorine or fluorine and the alkyl contain 1 to 4 carbon atoms.

20. A process according to claim 19 wherein the non-symmetrical ketene is (4-chlorophenyl)isopropylketene, (4-(difluoromethoxy)phenyl)isopropylketene, or ((4-trifluoromethyl-3-chlorophenyl)-(benzyloxycarbonyl)amino)isopropylketene.

21. A process according to claim 12 wherein the non-symmetrical ketene is prepared by treating an acid halide with a tertiary amine.

22. A process according to claim 21 wherein the acid halide is isopropyl-(4-chlorophenyl)acetyl chloride.

* * * * *